Figure 1:
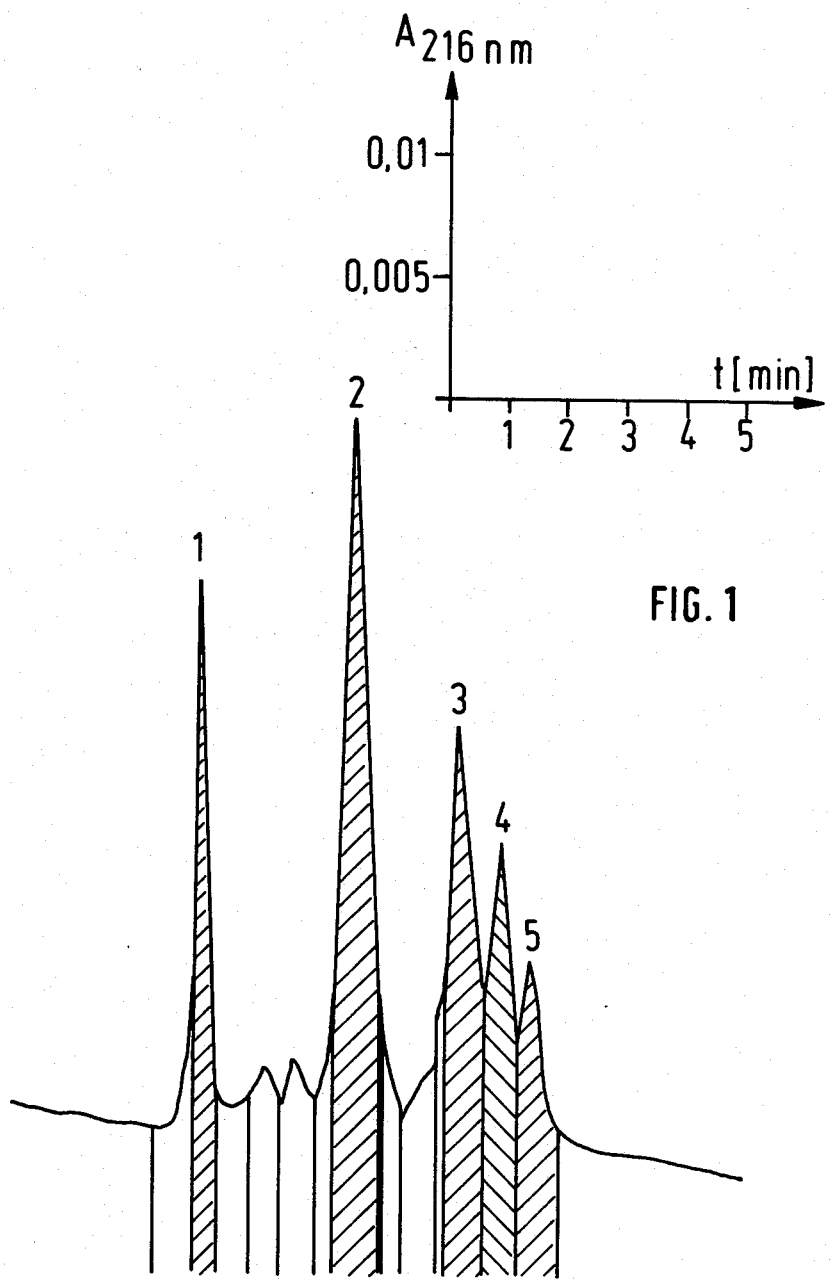

United States Patent [19]

Kramer et al.

[11] Patent Number: 4,791,100

[45] Date of Patent: * Dec. 13, 1988

[54] NOVEL POLYPEPTIDES WITH A BLOOD COAGULATION-INHIBITING ACTION, PROCESSES FOR THEIR PREPARATION AND ISOLATION, THEIR USE AND AGENTS CONTAINING THEM

[75] Inventors: Martin Kramer, Wiesbaden; Dominique Tripier, Eppstein, both of Fed. Rep. of Germany

[73] Assignee: Hoechst Aktiengesellschaft, Fed. Rep. of Germany

[*] Notice: The portion of the term of this patent subsequent to May 26, 2004 has been disclaimed.

[21] Appl. No.: 885,821

[22] Filed: Jul. 15, 1986

[30] Foreign Application Priority Data

Jul. 17, 1985 [DE] Fed. Rep. of Germany ....... 3525428
Jan. 16, 1986 [DE] Fed. Rep. of Germany ....... 3601032

[51] Int. Cl.$^4$ ...................... A61K 37/02; C07K 7/10
[52] U.S. Cl. ...................................... 514/12; 514/21; 530/324
[58] Field of Search ................. 530/324, 350; 514/12, 514/21

[56] References Cited

U.S. PATENT DOCUMENTS 4,654,302  3/1987  Fritz et al. .......................... 530/324
4,668,662  5/1987  Tripier ............................... 530/324

FOREIGN PATENT DOCUMENTS 0158986  10/1985  European Pat. Off. .
3342139   5/1985  Fed. Rep. of Germany .
8504418  10/1985  PCT Int'l Appl. .

OTHER PUBLICATIONS

Jutisz et al., Purification De L'Hirudine, Bull. Soc. Chim. Biol. vol. 45, No. 1, (1963), pp. 55-67.

Methods in Enzymology, vol. XLV, Part B (1975), pp. 669-678.

Markwardt et al., Reindarstellung und Analyse des Thrombininhibitors Hirudin, Hopp-Seyler's Z/Physiol. Chem., Bd. 348 (1967), pp. 1381-1386.

Primary Examiner—Delbert R. Phillips
Assistant Examiner—Christina Chan
Attorney, Agent, or Firm—Finnegan, Henderson, Farabow, Garrett, & Dunner

[57] ABSTRACT

The invention relates to a polypeptide of the formula

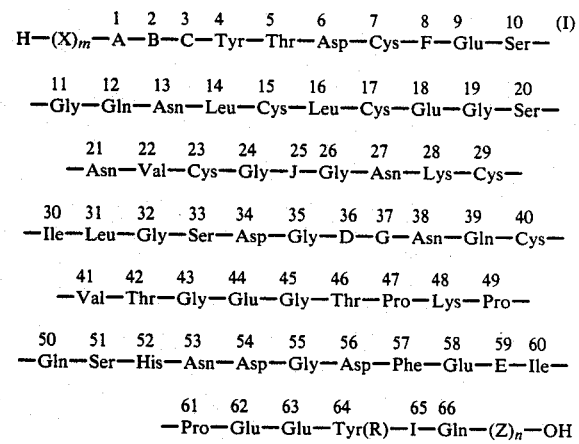

in which R represents phenoloic hydrogen or a phenolic ester group and m, n, X, Z, A, B, C, D, E, F, G, I and J have the meanings given, and in which the 6 Cys radicals are linked in pairs via disulfide bridges, processes for the preparation or isolation thereof, their use and agents containing them.

10 Claims, 9 Drawing Sheets

NOVEL POLYPEPTIDES WITH A BLOOD COAGULATION-INHIBITING ACTION, PROCESSES FOR THEIR PREPARATION AND ISOLATION, THEIR USE AND AGENTS CONTAINING THEM

Anticoagulants are used in the prophylaxis and therapy of thromboembolic processes; their main field of use here is, in particular, venous thromboembolisms. Anticoagulants are furthermore required for the preparation of conserved blood. Derivatives of 4-hydroxycoumarin or of 1,4-indanedione which are used, for example, for this purpose have a number of disadvantages, in spite of extensive optimization.

It is therefore desirable, especially in human medicine, to have available blood coagulation inhibitors which have a low toxicity and few side effects and which do not cause stress to the diseased organism because of their metabolism.

Apart from the endogenous inhibitors in the plasma, such as antithrombin III, many other proteins, such as, for example, the Kunitz inhibitor obtained from soybean, also have a blood coagulation-inhibiting action. This inhibitor blocks the blood coagulation cascade by inhibition of activated factor X, but the specificity of the inhibitor is so low that many side effects develop: inhibition of plasma kallikrein, of plasmin and of trypsin, so that therapeutic uses are excluded. Other active compounds, such as the Ascaris or Kazals inhibitor, have also been unable to achieve importance because of a lack of specificity.

Hirudin, a polypeptide obtained from *Hirudo medicinalis*, in contrast shows a specific antithrombin activity. The elaborate process for its isolation and purification has hitherto had adverse effects on its use in practice.

It has now been found that highly active polypeptides of the formula I can be isolated from leeches.

The invention therefore relates to polypeptides of the formula I

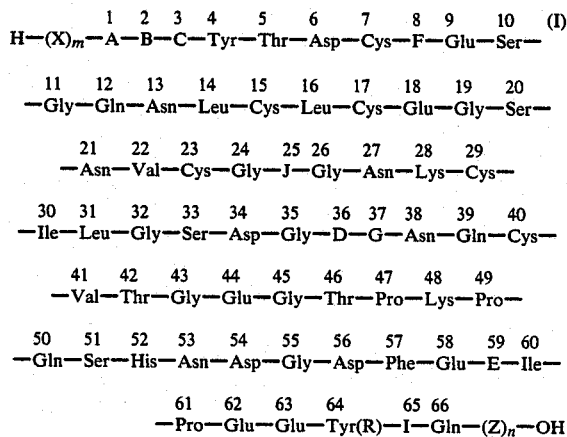

in which
m = 0–50,
n = 0–100 and
R denotes phenolic hydrogen or a phenolic ester group,
X represents identical or different radicals of naturally occurring α-amino acids,
Z represents identical or different radicals of naturally occurring α-amino acids and
A represents Ile or the absence of an amino acid,
B represents Ile or Thr or the absence of an amino acid,
C denotes Thr, Val, Ile, Leu or Phe,
D denotes Glu or the absence of an amino acid,
E denotes Glu or Pro,
F denotes Thr or Ile,
G denotes Lys or Lys-Asp and
I denotes Ala or Leu and
J denotes Gln or Lys
in which the 6 Cys radicals are linked in pairs via disulfide bridges, and physiologically acceptable salts thereof.

The three disulfide bridges are preferably between the Cys radicals in positions 7 and 15, 17 and 29 and 23 and 40.

Naturally occurring α-amino acids are, in particular, Gly, Ala, Ser, Thr, Val, Leu, Ile, Asp, Asn, Glu, Gln, Cys, Met, Arg, Lys, Hyl, Orn, Cit, Tyr, Phe, Trp, His, Pro and Hyp.

R preferably denotes hydrogen, $SO_3H$ or $PO_3H_2$; hydrogen is particularly preferred.

Possible salts are, in particular, alkali metal and alkaline earth metal salts, salts with physiologically acceptable amines and salts with physiologically acceptable acids, such as HCl, $H_2SO_4$, maleic acid or acetic acid.

Preferred polypeptides of the formula I are those in which C represents Thr; and furthermore those in which C represents Thr and A represents Ile. Particularly suitable peptides are those where A=Ile, B=Thr, C=Thr, D=Glu, E=Glu, F=Thr, G=Lys, I=Leu, J=Gln, m=zero, n=zero and R=H or $SO_3H$;

m=zero, n=zero, R=H or $SO_3H$, A=Ile, B=direct bond, C=Thr, D=Glu, E=Glu, F=Thr, G=Lys, I=Leu and J=Gln;

m=zero; n=zero; R=H or $SO_3H$, A=Ile, B=direct bond, C=Thr, D=Glu, E=Glu, F=Ile, G=Lys, I=Leu and J=Gln;

m=zero, n=zero, R=H or $SO_3H$, A=Ile, B=direct bond, C=Thr, D=Glu, E=Pro, F=Thr, G=Lys, I=Leu and J=Gln;

m=zero, n=zero, R=H or $SO_3H$, A=Ile, B=direct bond, C=Thr, D=Glu, E=Pro, F=Ile, G=Lys, I=Leu and J=Gln;

m=zero, n=zero, R=H or $SO_3H$, A=direct bond, B=direct bond, C=Thr, D=direct bond, E=Glu, F=Thr, G=Lys, I=Leu and J=Gln;

A=Ile, B=direct bond, C=Thr, D=direct bond, E=Glu, F=Ile, G=Lys-Asp, I=Ala, J=Lys, m=zero, n=zero and R=$SO_3H$;

A=Ile, B=direct bond, C=Thr, D=direct bond, E=Glu, F=Ile, G=Lys-Asp, I=Ala, J=Lys, m=zero, n=zero and R=hydrogen.

The invention also relates to the novel biologically active peptidic cleavage products which are obtained by chemical or enzymatic cleavage of these polypeptides.

The invention furthermore relates to a process for isolating a purified polypeptide of the abovementioned formula, which comprises isolating the polypeptide from worms of the phylum Annelida with the aid of a combination of extraction methods, precipitation methods, membrane filtration and/or chromatographic methods, if desired splitting off any phenolic ester group R which may be present by hydrolysis, to form the phenolic hydroxyl group, and, if appropriate, converting the resulting peptide into its physiologically acceptable salts.

The polypeptide is preferably isolated from the cervical glands of worms of the class Hirudinea, in particular from those of the order Gnathobdellida. The genuses Hirudo, Gnathobdella, Haemadipsa and Philaemon are preferred. Hirudo medicinalis is particularly preferred. In addition to the cervical glands of the leech, its front body region or the entire leech can also be used.

A process for isolation of a crude extract from leeches is described in Enzymology, Volume 5 "Hirudin as an Inhibitor of Thrombin". A purification process for hirudin is known from Bull. Soc. Chim. Biol. 45 (1963) 55.

In the process according to the invention, a combination of precipitation methods and of gel permeation chromatography or ultrafiltration, affinity chromatography and of high-resolution partition chromatography on "reverse phase" material and chromatography on silica gel or aluminum oxide has proved particularly useful. Depending on the nature of the crude extract, however, other chromatography processes can also advantageously be used (if necessary also in combination with the abovementioned process), such as, for example, cation or anion exchange chromatography and chromatography on non-specific absorbents, in particular hydroxyapatite.

In order to isolate a crude extract suitable for chromatography, the leeches can be worked up in the manner described by Bagdy et al. Methods of Enzymology 45 [1976] 669-678. However, it is also possible, for example, to comminute the head portions of the leech in the frozen state and extract them by means of an aqueous buffer solution (for example phosphate buffer). The insoluble material is removed, for example, by brief centrifugation or by filtration through gauze and the polypeptide is separated off from the resulting extract and isolated. It is advantageous to heat this extract rapidly to 70° to 90° C., because most of the proteolytic enzymes are thereby denatured and precipitate, and can then be separated off, for example by centrifugation. The protein fraction is isolated from the extract containing the peptide according to the invention, for example by precipitation by adding the extract to a water-miscible organic solvent. Acetone, for example, can be employed in an amount of several times the volume of extract, preferably in about 10 times the amount, precipitation being carried out at low temperatures, usually at 0° to −40° C., preferably at about −20° C.

Another possibility of carrying out the precipitation is the addition of salts, such as, for example, ammonium sulfate. By controlling the pH, precipitation achieves a certain selectivity. The peptides according to the invention, which have isoelectric points of 3.5-4, can be precipitated in the pH range between 3 and 5, preferably at about 4, by addition of ammonium sulfate up to a concentration of about 50%, a large number of concomitant proteins thereby remaining in solution. This precipitation is also carried out with cooling at about −5° to +15° C., preferably between 0° and +4° C.

Higher molecular weight proteins can be separated off from this crude extract, for example, by ultrafiltration or by gel permeation chromatography. In the case of larger batches, ultrafiltration can be carried out, for example, in two stages: a capillary membrane with an exclusion limit of 50,000 daltons is used in the first stage and a flat membrane with an exclusion limit of 10,000 daltons is then used in the second stage. Rapid removal of higher molecular weight material which would prevent flow through the selectively operating flat membrane is achieved with the aid of the capillary membrane. In the case of small amounts, it is also possible to dispense with the first ultrafiltration stage.

Purification of the crude extract can also be carried out by means of ion exchange chromatography, for example on DEAE-®Sephadex, in the manner described by Markwardt, Walsmann, Hoppe-Seyler's Z. Physiol. Chem. 348 [1967] 1381-1386.

The material thus obtained consists of a mixture of thrombin inhibitors according to the invention and other polypeptides. A preferred process for isolating the inhibitors of the formula I where $R=H$ or $SO_3H$ comprises separating the thrombin inhibitors, on the basis of their complexing properties with carrier-bound thrombin, from products which do not form complexes with thrombin. The fractions which have been obtained on the basis of their thrombin affinity can in turn be separated into individual components by a second high-resolution chromatographic system. The inhibitors of the formula I are thus isolated. It has proved particularly suitable to use thrombin-Sepharose for affinity chromatography. Thrombin-Sepharose was prepared by the Brosstad process (Thrombos Res. II, 119, 1977).

For the separation, thrombin-Sepharose is poured into a column with a suitable buffer, such as, for example, 0.1M N-methylmorpholine acetate buffer, pH 8.0, or Tris/HCl, 0.1M, pH 8.5. After equilibration of the column, the mixture from the precipitation is dissolved in the same buffer and applied to the column. The peptides which have no thrombin affinity are removed by washing with the buffer. Thereafter, the thrombin/thrombin inhibitor complex is resolved by washing the column with a buffer of 0.5-2M benzamidine or 4-amino-benzamidine in 0.1M N-methylmorpholine acetate, pH 8.0. The various active fractions are pooled together and salts are removed by customary gel permeation chromatography on Sephadex G 25 with 0.05M N-methylmorpholine acetate, pH 8.0.

The various thrombin inhibitors are separated from one another by high-resolution chromatographic processes. High performance liquid chromatography has proved particularly suitable for this.

Due to the high resolution capacity of high performance liquid chromatography technology, it is possible to separate the inhibitors of the formula I from one another and from small amounts of concomitant protein and to prepare them in a pure form.

Derivatized silica gels of suitable particle size (for example between 3 and 20 μm) have proved advantageous for the stationary phase. In addition to the widely used octadecylsilane radicals, a large number of other silane radicals or mixtures thereof, such as silane radicals with lower alkyl, phenylalkyl or amino-substituted alkyl are suitable for derivatization of the silica gel, the latter radicals offering a certain combination of ion exchange and "reverse phase" chromatography. Separation columns 5 to 25 cm long and 3 to 10 mm in diameter, for example, can be used. Possible buffered eluting agents are all the secondary or tertiary mixtures of water and organic solvents of suitable lipophilicity, such as, for example, lower alcohols, ketones, nitriles, ethers, acid, amines, glycol ethers, amides and derivatives thereof. Organic and inorganic salts or other types of additives can be used as the buffer substance. The elution is advantageously carried out at a pH between 2 and 8.

The use of volatile buffer substances, such as ammonium acetate or ammonium bicarbonate, enables the inhibitors to be isolated from the eluate by simple freeze-drying.

A sulfate monoester group R in position 64 can be split off by acid catalysis or enzymatically with the aid of an arylsulfatase, in a manner analogous to that described in German Pat. No. A-3,342,139.

The polypeptides of the formula I according to the invention are colorless and soluble in water and in aqueous buffers, manifest themselves as homogeneous in polyacrylamide electrophoresis and have isoelectric points of 3.5 to 4 (determined by isoelectric focussing). If the amino acid composition is determined by the method of Moore and Stein (Methods of Enzymology Volume VI, 819–831, published by Rolovick and Kaplan, Academic Press, New York, London, 1963), the values shown in Table 1 are found.

TABLE 1

|  | II | III | IV | V | VI | VII | VIII | IX |
|---|---|---|---|---|---|---|---|---|
| Aspartic acid | 9 | 9 | 9 | 9 | 9 | 9 | 10 | 10 |
| Threonine | 6 | 5 | 4 | 5 | 4 | 5 | 4 | 4 |
| Serine | 4 | 4 | 4 | 4 | 4 | 4 | 4 | 4 |
| Glutamic acid | 13 | 13 | 13 | 12 | 12 | 12 | 11 | 11 |
| Proline | 3 | 3 | 3 | 4 | 4 | 3 | 3 | 3 |
| Glycine | 9 | 9 | 9 | 9 | 9 | 9 | 9 | 9 |
| Valine | 2 | 2 | 2 | 2 | 2 | 2 | 2 | 2 |
| Cysteine | 6 | 6 | 6 | 6 | 6 | 6 | 6 | 6 |
| Isoleucine | 3 | 3 | 4 | 3 | 4 | 2 | 4 | 4 |
| Leucine | 4 | 4 | 4 | 4 | 4 | 4 | 3 | 3 |
| Tyrosine | 2 | 2 | 2 | 2 | 2 | 2 | 2 | 2 |
| Phenylalanine | 1 | 1 | 1 | 1 | 1 | 1 | 1 | 1 |
| Lysine | 3 | 3 | 3 | 3 | 3 | 3 | 4 | 4 |
| Histidine | 1 | 1 | 1 | 1 | 1 | 1 | 1 | 1 |
| Alanine | 0 | 0 | 0 | 0 | 0 | 0 | 1 | 1 |

IX is obtained by desulfation of VIII.

The invention furthermore relates to a process for the preparation of a polypeptide of the abovementioned formula I, which comprises (a) preparing it by means of solid phase synthesis in a manner which is known per se or
(b) to prepare a polypeptide in which m is 0,
   I. subjecting hirudin to Edman degradation twice,
   II. reacting the resulting peptide with an active ester of an amino acid or of a peptide of the formula

   U—(X)$_m$—A—B—C—OH in which m, X, A, B and C are as defined above and U represents a urethane protective group which is unstable to acids or bases,
   III. splitting off the phenylthiocarbamoyl group on the ε-amino group of Lys by means of hydrazine
   IV. and the urethane protective group U with the aid of an acid or base and
   if appropriate, converting the polypeptide obtained by (a) or (b) into its physiologically acceptable salt.

In the solid phase synthesis (in this context, cf. Atherton, Sheppard, Perspectives in Peptide Chemistry, Karger Basel 1981, pages 101–117), an OH-protective group for Thr can as a rule be dispensed with.

The polypeptide of the formula I is synthesized, for example, stepwise on hydroxymethylated polystyrene resin. The polystyrene is crosslinked with, for example, 1% of divinylbenzene. It is usually in the form of small beads.

The amino acids are used with N-terminal protection. The first N-protected amino acid is attached to the carrier by ester formation. After removal of the amino-protective group, the next N-protected amino acid is attached using a coupling reagent, such as dicyclohexylcarbodiimide. Removal of the protection and addition of further amino acids is continued until the desired sequence is achieved.

The choice of protective groups depends on the amino acids and coupling methods.

Possible amino-protective groups are, for example, the known urethane protective groups, such as benzyloxycarbonyl(Z), p-methoxycarbobenzoxy, p-nitrocarbobenzoxy, t-butyloxycarbonyl(Boc), Fmoc and the like.

The Boc group is preferred, since it can be split off under relatively mild conditions (for example with trifluoroacetic acid or HCl in organic solvents).

Threonine can be blocked as the benzyl ether, and the ε-amino group of lysine can be blocked as the Z derivative.

These two protective groups are largely resistant towards the reagents for splitting off the Boc group and can be removed hydrogenolytically with a hydrogenation catalyst (Pd/active charcoal) or, for example, with sodium in liquid ammonia.

The protected peptide can be removed from the resin with, for example, hydrazine. The hydrazide is thereby formed, and can be converted into the free carboxylic acid with, for example, N-bromosuccinimide in accordance with the method of Int. J. Pept. Prot. Research 17 (1981) 6–11. If necessary, the disulfide bridges must be closed oxidatively (cf. Konig, Geiger, Perspectives in Peptide Chemistry, Karger Basel pages 31–44).

In process variant (b), hirudin is subjected to Edman degradation twice, this polypeptide being reacted with an isothiocyanate, preferably phenyl isothiocyanate, in a suitable buffer solution, such as pyridine/water or dioxane/water, if appropriate with the addition of a base, such as dimethylbenzylamine (DMBA), dimethylallylamine (DMAA) or triethylamine, preferably at about 50° C. and at a pH of 8–9. After removal of the excess buffer and the excess phenyl isothiocyanate, the N-terminal valine is split off as phenylthiazolinone by treatment with an acid (heptafluorobutyric acid or trifluoroacetic acid) at 50° C. for 10 minutes. This reaction sequence is repeated for the cleavage of the second valine on the N-terminus.

The de-(Val)$_2$-hirudin derivative obtained in this manner is reacted with an active ester of an amino acid or of a peptide of the formula U—(X)$_m$—A—B—C—OH. p-Nitrophenyl-, cyanomethyl- or N-hydroxyphthalimide or, in particular, N-hydroxysuccinimide esters, for example, are suitable. Suitable urethane protective groups U are those which can be split off under acid or alkaline conditions, such as, for example, Boc or Msc. If necessary, any groups present in the side chains of B and C can also be temporarily protected by suitable protective groups.

The protected precursor of the polypeptide of the formula I (m=0) which is obtained in this manner is treated with hydrazine hydrate in a suitable solvent, such as a lower alcohol or a mixture thereof with water, to split off the phenylthiocarbamoyl group on the lysine.

The remaining protective group(s) is/are now also split off from this polypeptide in a suitable manner (Boc with, for example, trifluoroacetic acid, Msc with a base), and the polypeptide of the formula I according to the invention is thus obtained.

The polypeptides according to the invention are specific stoichiometric inhibitors of thrombin. Quantitative measurement of the thrombin inhibition by the inhibitors according to the invention has shown that the thrombin inhibitor/thrombin complex is virtually undissociated. The activity and thus the degree of purity of the polypeptides according to the invention can be determined with the aid of this measurement method during working up and purification. These polypeptides of the abovementioned formula I thus purified can have a thrombin inhibition of more than 10,000 antithrombin units/mg and hence exceed that of conventional hirudin. These compounds of the formula I with free phenolic hydrogen in position 64 are as a rule even more active in vivo.

The invention therefore also relates to the use of polypeptides of the formula I in which m, n, R, X, Z, A, B, C, D, E, F, G, J and I have the abovementioned meaning as blood coagulation inhibitors for use in the therapy of thromboembolic processes, and to the use thereof as diagnostic aids and reagents.

The invention furthermore relates to agents which contain a polypeptide of the formula I or a peptidic cleavage product thereof in a pharmaceutically acceptable excipient.

The compounds according to the invention can be administered parenterally or topically in a corresponding pharmaceutical formulation.

For subcutaneous or intravenous administration, the active compounds or physiologically acceptable salts thereof are dissolved, suspended or emulsified, if appropriate with the substances customary for this, such as solubilizing agents, emulsifiers, isotonicity agents, preservatives or other auxiliaries. Possible solvents for the novel active compounds and the corresponding physiologically acceptable salts are, for example: water, physiological sodium chloride solutions or alcohols, for example ethanol, propanediol or glycerol, and in addition also sugar solutions, such as glucose solutions or mannitol solutions, or a mixture of the various solvents mentioned. On subcutaneous use, compounds of the formula I (R=phenolic hydrogen) as a rule have the advantage of a slower absorption and hence a delayed action.

The topical excipients can be organic or inorganic compounds. Typical excipients used pharmaceutically are aqueous solutions which are, for example, buffer systems or isotonic mixtures of water and water-miscible solvents, such as, for example, alcohols or aryl alcohols, oils, polyalkylene glycols, ethylcellulose, carboxymethylcellulose, polyvinylpyrrolidone or isopropyl myristate. Suitable buffer substances are, for example, sodium borate, sodium phosphate, sodium acetate or gluconate buffer. The topical use form can also contain non-toxic auxiliaries, such as, for example, emulsifying preservatives, crosslinking agents, such as, for example, polyethylene glycols, and antibacterial compounds.

EXAMPLE 1

Determination of the inhibitor concentration by thrombin titration

200 μl of sodium bicarbonate solution (pH=7.0; 0.5M) are added to 10 to 100 μl of the inhibitor solution with a previously determined protein content. 0.1 ml of fibrinogen solution (0.5 to 1% strength) or dilute citrate plasma are added; an aliquot (50–100 μl) of the thrombin solution is added (about 100 NIH units per ml) at regular intervals, while stirring, at room temperature. The endpoint can be the coagulation of the liquid within the chosen interval of time for the semi-quantitative procedure or turbimetry measurement at 546 nm for quantitative determination.

EXAMPLE 2

Free-living leeches (not bred animals) of the species Hirudo medicinalis which have been collected in Germany are used.

About 150–200 g of the front portions of frozen leeches are homogenized with 2 liters of ice-cold 0.09% strength aqueous sodium chloride solution and 10 ml of octanol in a mixer in the course of 3 minutes. After centrifugation at 0° C. and 10,000 revolutions per minute for 30 minutes, the supernatant is clarified further by filtration through 2 layers of gauze and then heated to 80° C. in the course of 15 minutes, while stirring. The precipitate formed is separated off by filtration through 4 layers of gauze. The filtrate is rapidly cooled to 4° C. by stirring in an ice-bath and is introduced into 7.5 liters of precooled acetone ($-20°$ C.). A precipitate again forms, and is filtered off on a glass suction filter after 5 minutes and rinsed with 1 liter of cold acetone ($-20°$ C.). After drying in vacuo, 520 mg of a pale yellowish powder with a protein content of 62% (determined by the Lowry method) are formed.

The antithrombin activity is about 400 units per mg.

EXAMPLE 3

520 mg of powder according to Example 2 are dissolved in 75 ml of water, the pH is then brought to 8.0 with 5N ammonia and the mixture is stirred at 0°–4° C. for 1 hour. The undissolved portion is centrifuged down with a cup centrifuge at 5,000 revolutions per minute in the course of 30 minutes. After adjusting the protein content to 25 mg/ml (Lowry) by addition of water, 35 ml of saturated ammonium sulfate solution are added to the solution and the mixture is stirred at 4° C. for 1 hour. The first precipitate is separated off rapidly by centrifugation (5,000 revolutions per minute/30 minutes). About a further 26 g of ammonium sulfate are dissolved in the supernatant and the pH is brought to 4 with glacial acetic acid. After standing for 5 hours, the entire suspension is centrifuged and the resulting moist precipitate is further processed as follows.

EXAMPLE 4

The moist precipitate obtained according to Example 3 is dissolved in 200 ml of 0.1M ammonium bicarbonate solution of pH 8 and the solution is subjected to ultrafiltration in a 250 ml Amicon ® cell with a 5PM 10 flat membrane (exclusion limit 10,000 daltons). The solution is thereby concentrated to about 40 ml, and towards the end is topped up twice with 150 ml of 0.1M ammonium bicarbonate solution of pH 8.0. Freeze-drying of the residue gives about 350 mg of material with a protein content of 89%.

EXAMPLE 5

Thrombin-Sepharose in 0.1M tris buffer (HCl), pH 8, is poured into a column (0.9×15 cm). The substance from Example 3 is dissolved in the same buffer and the column is charged with this sample. Inactive concomitant substances are removed by rinsing the column with the equilibration buffer. Thereafter, the hirudin can be displaced from the thrombin-hirudin complex with a solution of benzamidine (1.5M tris buffer, pH 7) or with 4-amino-benzamidine (0.2M tris buffer, pH 7) and is eluted in portions. To test the antithrombin activity, the competitive inhibitor must first be separated from the hirudin by gel filtration on ®Sephadex G 20.

```
I T Y T D C T E S G Q N L C L C E G S N V C G Q G N K
C I L G S D G E K N Q C V T G E G T P K P Q S H N D G D
F E E I P E E Y L Q.
```

Yield in weight: 55%;
Activity: 6,000 to 12,000 ATU/mg.

EXAMPLE 6

20 mg of inhibitor according to Example 3 are dissolved in 200 µl of water of pH 2.16 (established with trifluoroacetic acid+5% of acetonitrile) and the solution is injected onto a steel column packed with octadecylsilanesilica gel (5 µm) (Shandon ®ODS). The column is eluted by a gradient of not more than 2%/minute between the starting buffer (water-pH=2.16+5% of acetonitrile) and acetonitrile. The fractions are collected individually. After drying, the inhibitors of the formula I (R=H or SO₃H) according to the invention have a specific activity which corresponds to the stoichiometry of a 1:1 complex with thrombin.

EXAMPLE 7

(a) The material obtained according to Example 4 was purified on DEAE- ®Sephadex A-25 in the manner described by Markwardt, Walsmann, Hoppe-Seyler's Z. Physiol. Chem. 348 [1967] 1381–1386.

(b) 1.1 mg of the protein fraction thus obtained was separated by means of high performance liquid chromatography on a 25 cm×4.6 mm ®Bio-Rad (Richmond, CA) Hi-Pore column packed with C-18 reverse phase silica gel with a particle size of 5µ and a pore width of 330 Å. 10% of acetonitrile in water with 0.1% of trifluoroacetic acid (A)/10% of water in acetonitrile with 0.1% of trifluoroacetic acid (B) was used as the mobile phase at a gradient rate of A:B of 1%/minute. The course of the chromatography with respect to time was monitored by detection at 216 nm (see FIG. 1).

The shaded fractions 1–5 in FIG. 1 were rechromatographed again, the same high performance liquid chromatography system being used.

Figure 2:
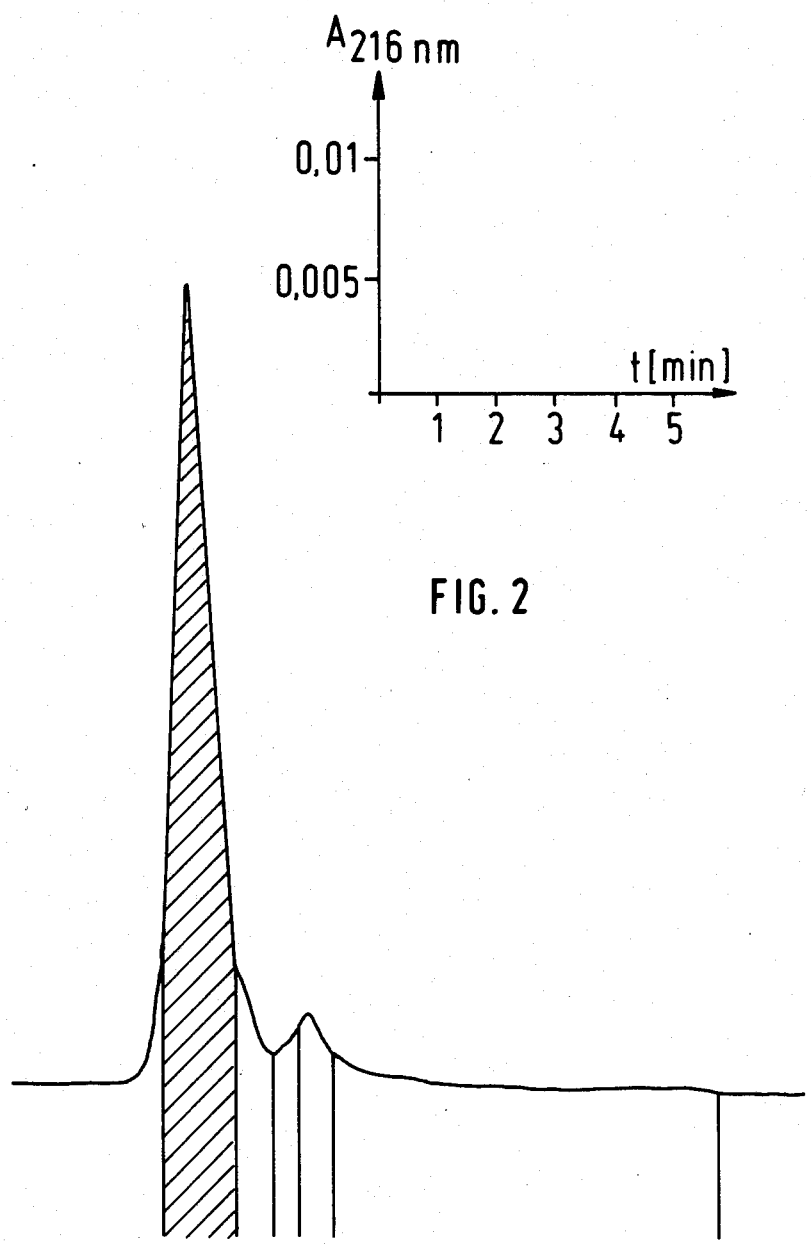

(c) Rechromatography of fraction 1 (FIG. 2) gave about 200 µg of a protein, the structure of which was determined by sequence analysis. It is assigned the following structure:

```
I T Y T D C T E S G Q N L C L C E G S N V C G Q G N K
C I L G S D G E K N Q C V T G E G T P K P Q S H N D G D
F E E I P E E Y L Q.
```

Figure 3:
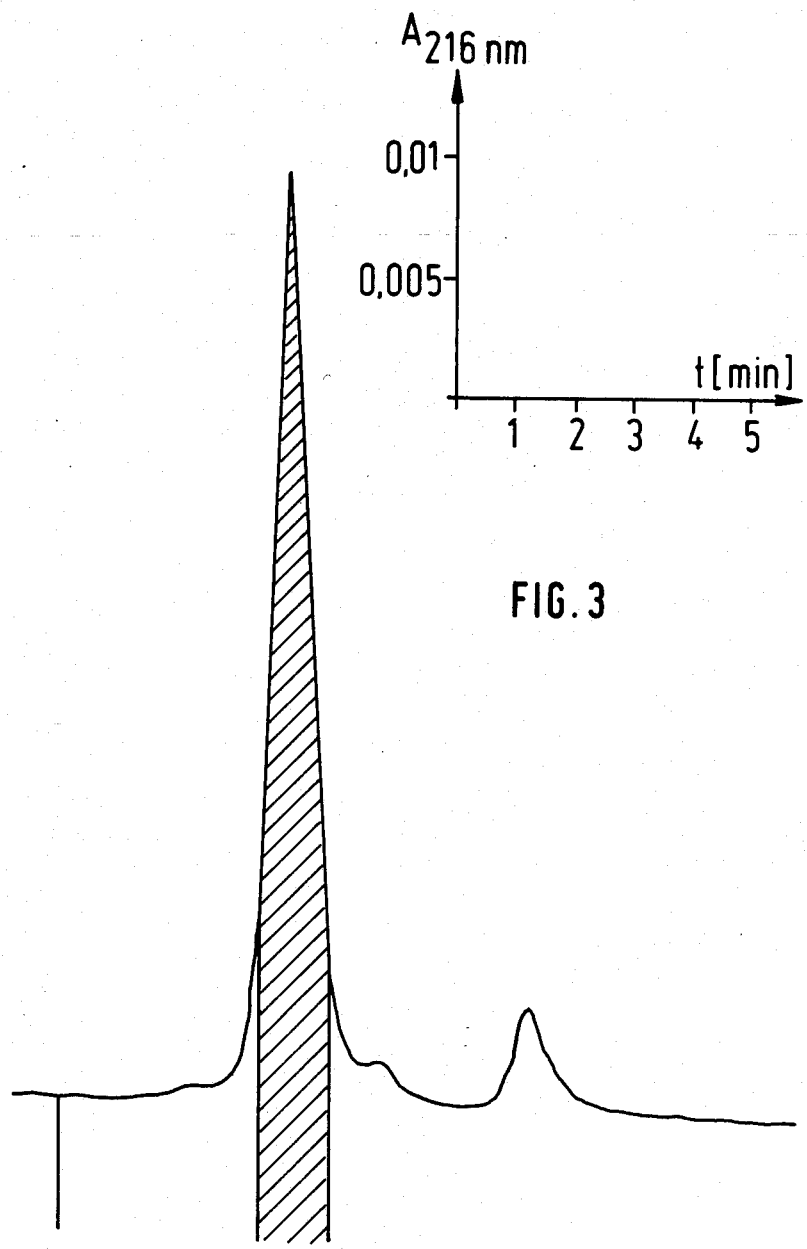

(d) Rechromatography of fraction 2 (FIG. 3) gave about 300 µg of a protein, the structure of which was determined by sequence analysis. It is assigned the following structure:

```
I T T Y T D C T E S G Q N L C L C E G S N V C G Q G N
K C I L G S D G E K N Q C V T G E G T P K P Q S H N D
G D F E E I P E E Y L Q.
```

Figure 4:
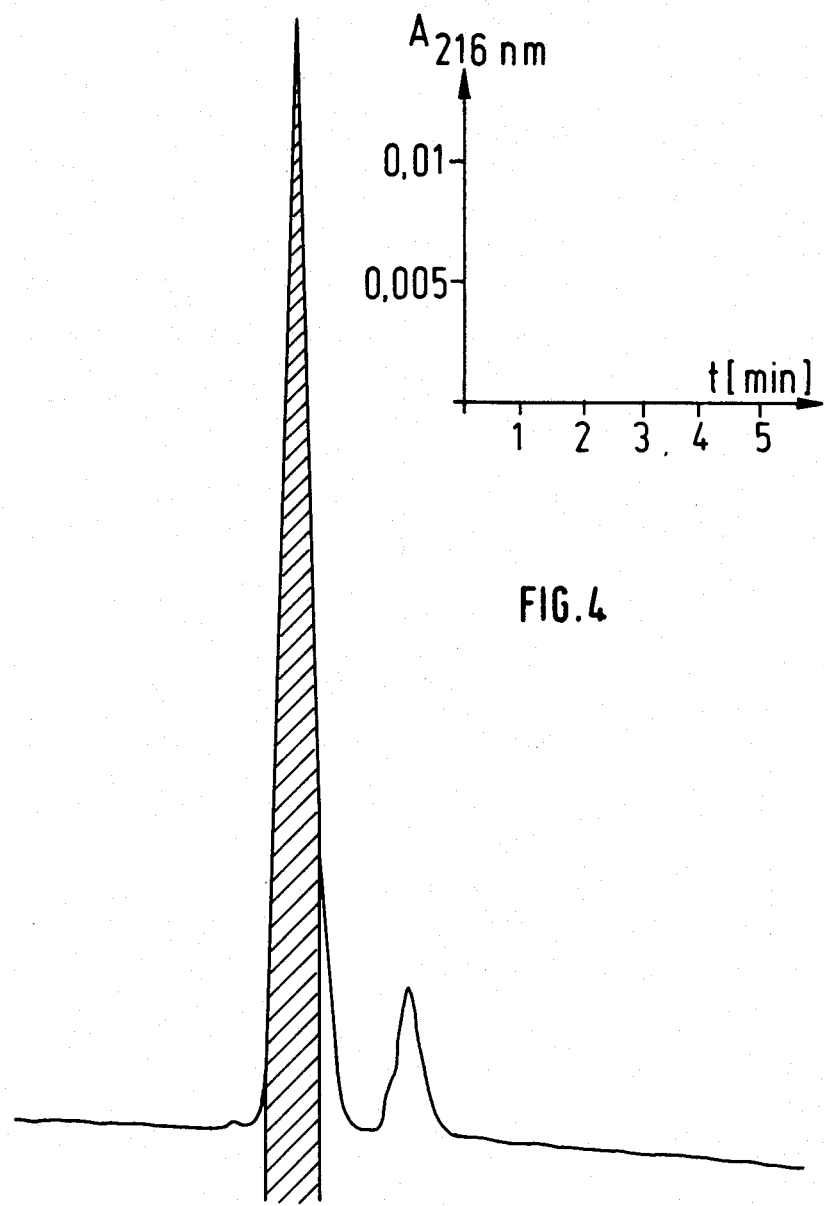

(e) Rechromatography of fraction 3 (FIG. 4) gave about 150 µg of a protein, the structure of which was determined by sequence analysis. It is assigned the following structure:

```
T Y T D C T E S G Q N L C L C E G S N V C G Q G N K C
I L G S D G E K N Q C V T G E G T P K P Q S H N D G D
F E E I P E E Y L Q.
```

Figure 5:
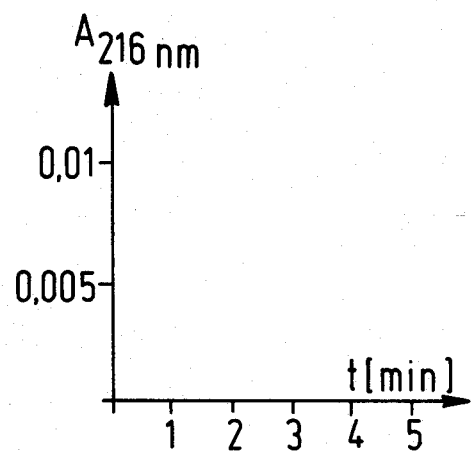
Figure 5:
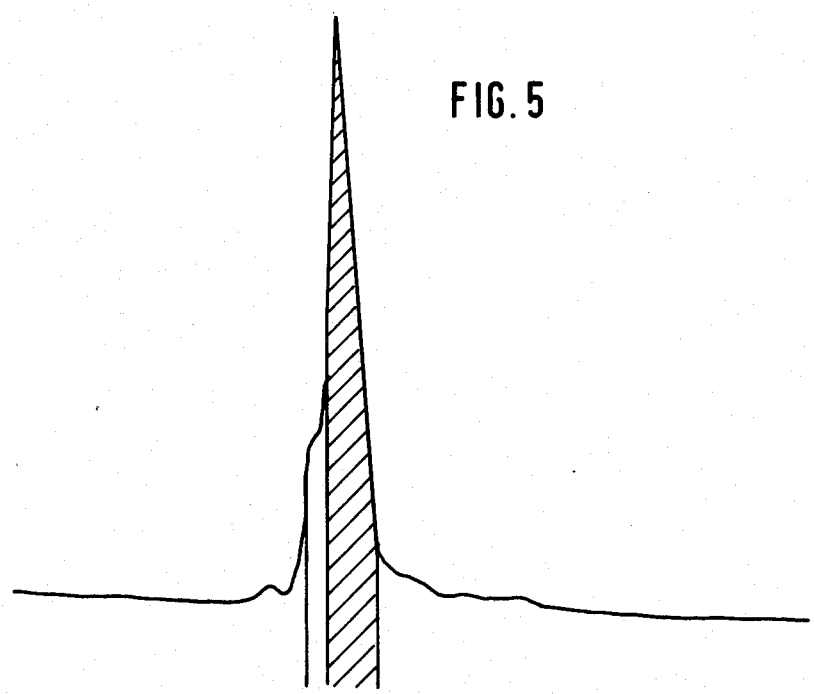

(f) Rechromatography of fraction 4 (FIG. 5) gave about 80 µg of a protein, the structure of which was determined by sequence analysis. It is assigned the following structure:

```
I T Y T D C I E S G Q N L C L C E G S N V C G Q G N K
C I L G S D G E K N Q C V T G E G T P K P Q S H N D G
D F E E I P E E Y L Q.
```

Figure 6:
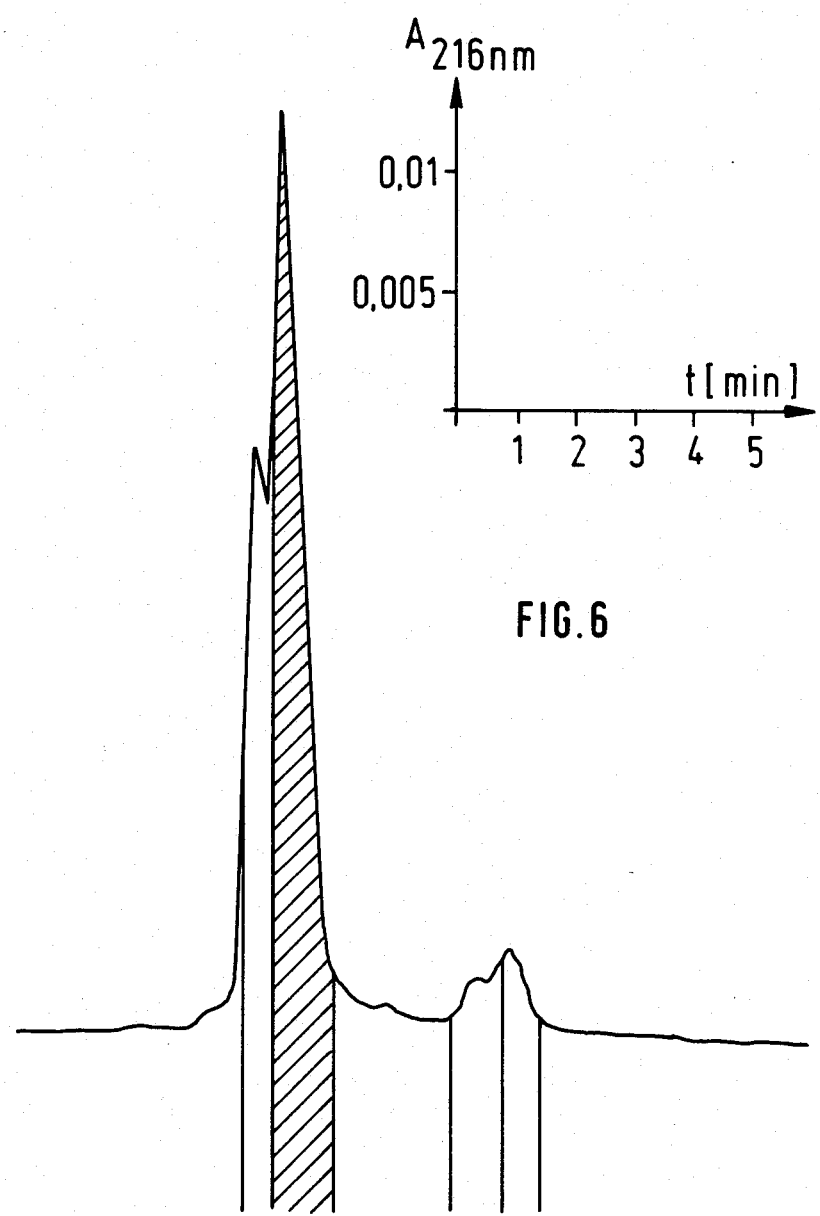

(g) Rechromatography of fraction 5 (FIG. 6) gave about 40 µg of a protein, the structure of which has not yet been determined.

EXAMPLE 8

(a) A material which had been obtained according to Example 5 by working up commercially available animals was used as the starting material and was subjected to prepurification according to Example 7(a).

Figure 7:
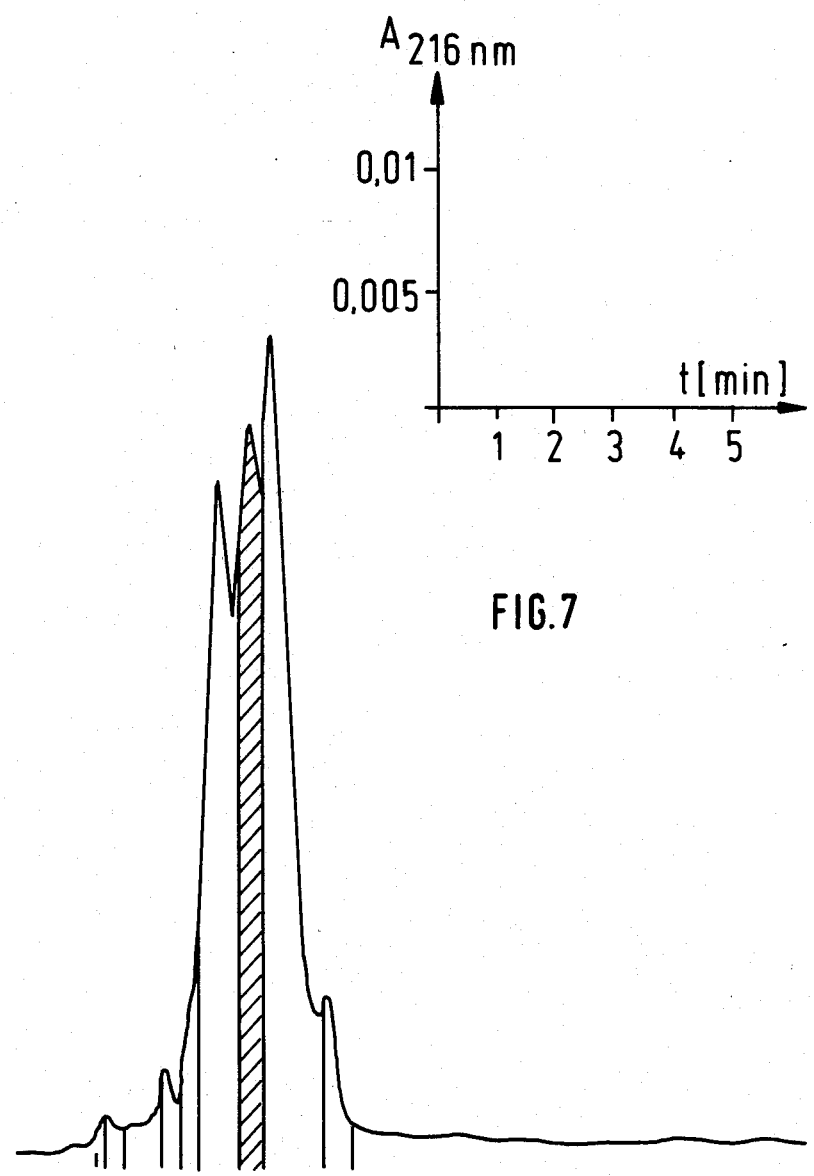
Figure 8:
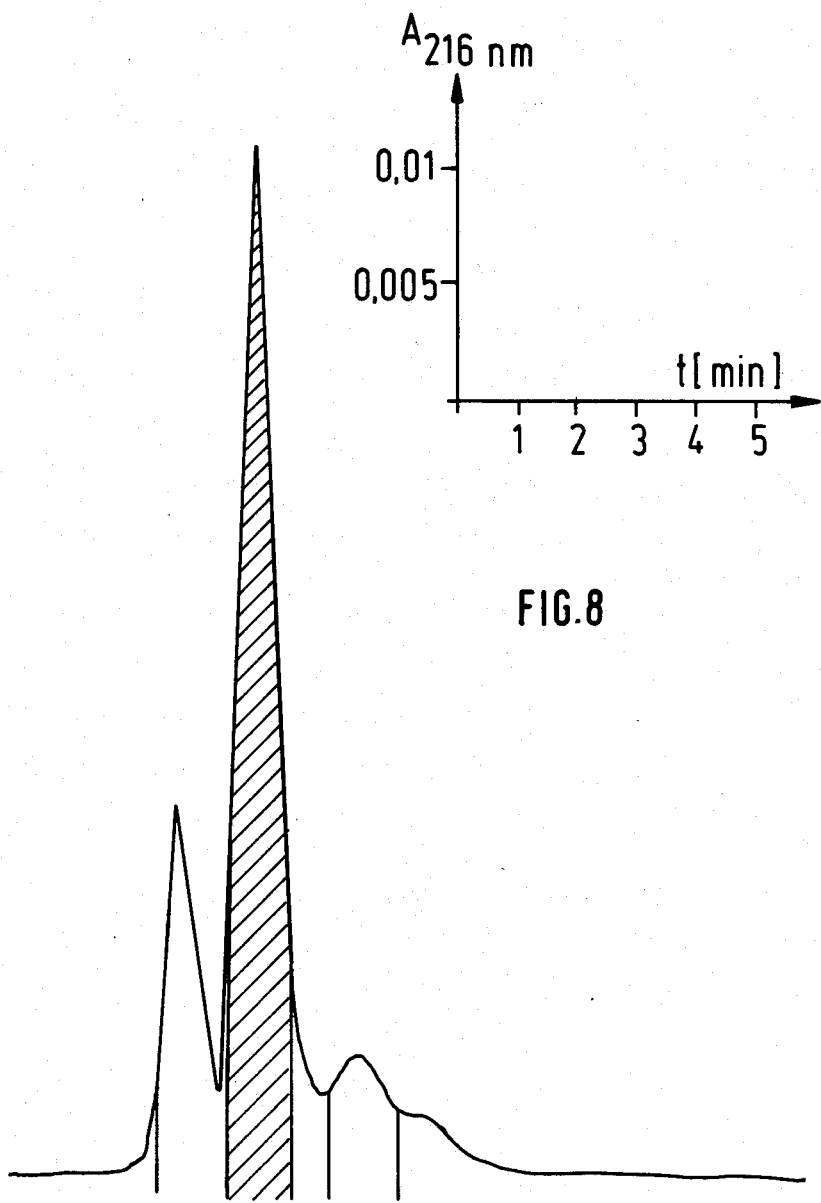
Figure 9:
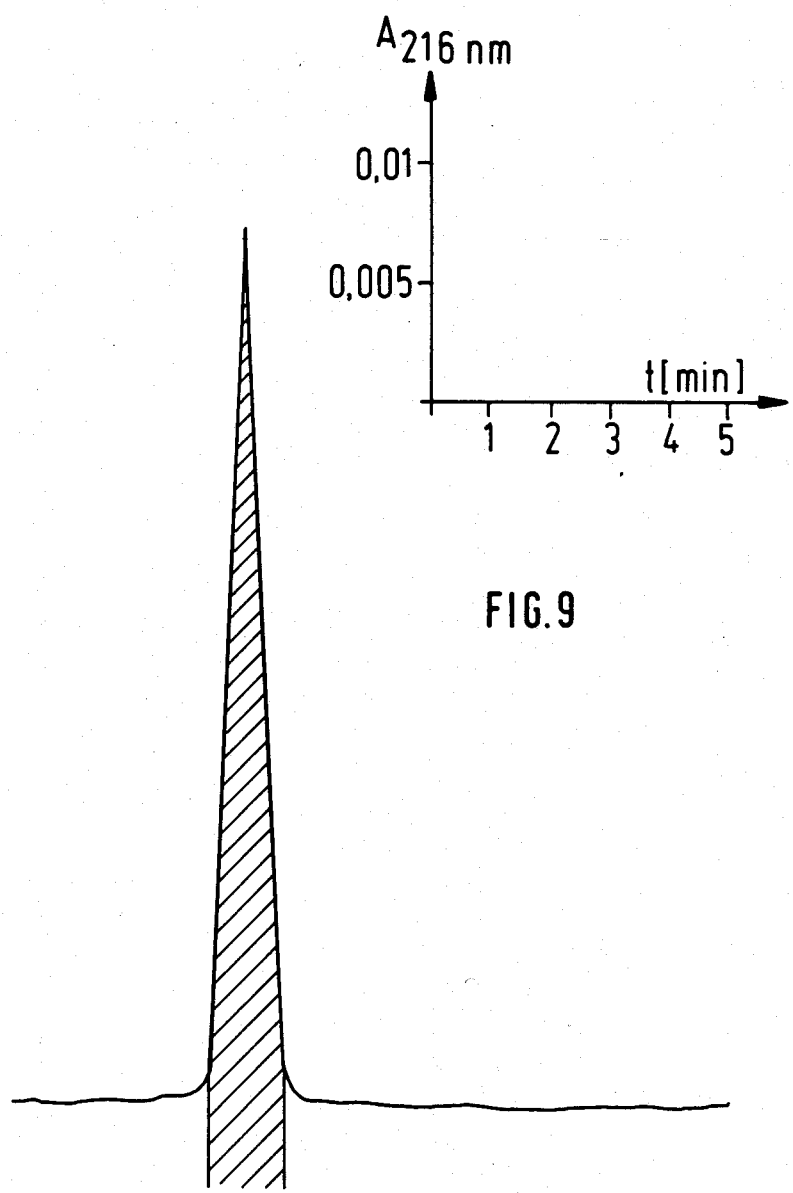

(b) 1 mg of the protein fraction thus obtained was fractionated by means of high performance liquid chromatography as in Example 7(b). The shaded fraction in FIG. 7 was rechromatographed, the conditions being the same, apart from a gradient rate of A:B of 0.8%/minute (FIG. 8). FIG. 9 shows the chromatogram of the analytically pure protein thus obtained, which is assigned the following structure, determined by sequence analysis:

```
I T Y T D C I E S G Q N L C L C E G S N V C G K G N K
C I L G S D G K D N Q C V T G E G T P K P Q S H N D G
D F E E I P E E Y A Q.
```

| Three- and one-letter symbols of the amino acids | | | |
|---|---|---|---|
| Amino acid | Abbreviation | Amino acid | Abbreviation |
| Alanine | Ala (A) | Proline | Pro (P) |
| Arginine | Arg (R) | Serine | Ser (S) |
| Cysteine | Cys (C) | Threonine | Thr (T) |
| Glycine | Gly (G) | Tryptophan | Trp (W) |
| Histidine | His (H) | Tyrosine | Tyr (Y) |
| Isoleucine | Ile (I) | Valine | Val (V) |
| Leucine | Leu (L) | Aspartic acid | Asp (D) |

| Three- and one-letter symbols of the amino acids | | | |
|---|---|---|---|
| Amino acid | Abbreviation | Amino acid | Abbreviation |
| Lysine | Lys (I) | Asparagine | Asn (N) |
| Methionine | Met (M) | Glutamic acid | Glu (E) |
| Phenylalanine | Phe (F) | Glutamine | Gln (Q) |

We claim:

1. A polypeptide of the formula I

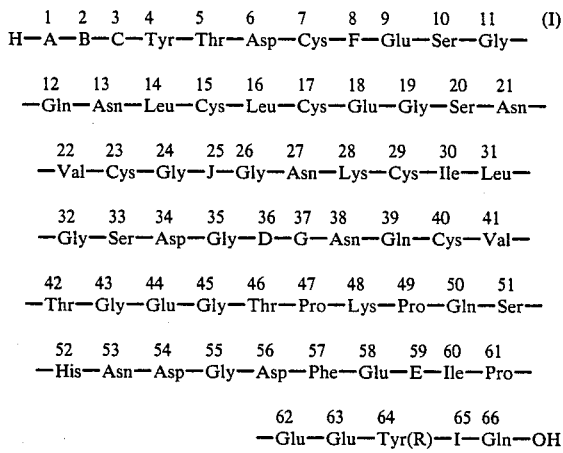

wherein

R represents a phenolic hydrogen or a phenolic ester group,

A represents Ile or the absence of an amino acid,

B represents Ile or Thr, or the absence of an amino acid,

C represents Thr, Val, Ile, Leu or Phe,

D represents Glu or the absence of an amino acid,

E represents Glu or Pro,

F represents Thr or Ile,

G represents Lys or Lys-Asp,

I represents Ala or Leu and

J represents Gln or Lys, provided that when A and B represent the absence of an amino acid, D represents the absence of an amino acid, E represents Pro, F represents Ile, G represents Lys-Asp, I represents Ala, or J represents Lys and wherein 7    15  17   29   23    40
Cys and Cys, Cys, and Cys, and Cys and Cys are linked in pairs via disulfide bridges, or a physiologically acceptable salt thereof.

2. A polypeptide as claimed in claim 1, in which C is Thr.

3. A polypeptide as claimed in claim 2, in which A is Ile.

4. A compound as claimed in claim 1, in which R denotes hydrogen, SO$_3$H or PO$_3$H$_2$.

5. A compound as claimed in claim 1, in which R represents SO$_3$H.

6. A compound as claimed in claim 1, in which R represents phenolic hydrogen.

7. A method for the prophylaxis and therapy of thromboembolic processes, which comprises administering to a mammal a pharmacologically active amount of a polypeptide of the formula I as claimed in claim 1 or a physiologically acceptable salt thereof.

8. A pharmaceutical formulation for the prophylaxis and therapy of thromboembolic processes comprising a pharmacologically active amount of a polypeptide of the formula (I) as claimed in claim 1 or a physiologically acceptable salt thereof and a physiologically acceptable excipient.

9. A method for the prophylaxis and therapy of thromboembolic processes, which comprises administering to a mammal a pharmacologically active amount of a polypeptide of the formula I as claimed in claim 1 or a physiologically acceptable salt thereof.

10. A pharmaceutical formulation for the prophylaxis and therapy of thromboembolic processes comprising a pharmacologically active amount of a polypeptide as claimed in claim 1 or a physiologically acceptable salt thereof and a physiologically acceptable excipient.

* * * * *